United States Patent

Metcalf et al.

[11] 3,939,277
[45] Feb. 17, 1976

[54] INSECTICIDAL BIODEGRADABLE ANALOGUES OF DDT

[75] Inventors: Robert L. Metcalf; Inder Kapoor; Asha Hirwe, all of Urbana, Ill.

[73] Assignee: The University of Illinois Foundation, Urbana, Ill.

[22] Filed: Sept. 6, 1973

[21] Appl. No.: 394,568

Related U.S. Application Data

[62] Division of Ser. No. 147,247, May 26, 1971, Pat. No. 3,787,505.

[52] U.S. Cl. ............... 424/340; 424/337; 424/354
[51] Int. Cl.² ................................... A01N 9/24
[58] Field of Search ............... 424/340; 260/612 R

[56] References Cited
UNITED STATES PATENTS

| | | | |
|---|---|---|---|
| 3,642,910 | 2/1972 | Holan | 260/613 R |
| 3,787,505 | 1/1974 | Metcalf et al. | 260/612 R |

OTHER PUBLICATIONS
Chemical Abstracts 41: 3571–3573 (1947).
Schneller et al. J.A.C.S. Vol. 70, pp. 4057–4059 (1948).

Primary Examiner—Leonard Schenkman
Attorney, Agent, or Firm—Merriam, Marshall, Shapiro & Klose

[57] ABSTRACT

Asymmetrical, biodegradable insecticides having the formula:

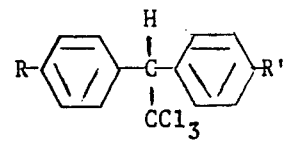

where R and R' are different and R is selected from the group consisting of $-CH_3$, $-CH_3O$, $-C_2H_5O$, $-C_3H_7O$, and R' is selected from the group consisting of $-SCH_3$, and $-CH_3$; and methods for providing and selectively controlling the biodegradability of DDT analogue insecticides.

4 Claims, No Drawings

INSECTICIDAL BIODEGRADABLE ANALOGUES OF DDT

This is a division of application Ser. No. 147,247, filed May 26, 1971, now U.S. Pat. No. 3,787,505.

SUMMARY OF THE INVENTION

The present invention relates to improved insecticides. In general, it concerns highly insecticidal, yet biodegradable compositions which exhibit low toxicity to mammals. More particularly, it pertains to such asymmetrical, biodegradable insecticides having the formula:

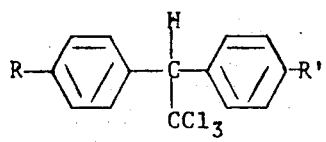

where R and R' are different and R is selected from the group consisting of —CH$_3$, —CH$_3$O, —C$_2$H$_5$O, —C$_3$H$_7$O, and R' is selected from the group consisting of —SCH$_3$, and —CH$_3$. The invention also pertains to methods for providing and selectively controlling the biodegradability of DDT analogue insecticides.

BACKGROUND OF THE INVENTION

Despite the immense utility of DDT 1,1,1-trichloro-2,2-bis(p-chlorophenyl)ethane as an insecticide, its usefulness is prejudiced by its environmental stability and low degree of biodegradability. There is growing concern about the continuing liberation of vast quantities of DDT into the environment. The very qualities which make DDT such an effective contact or residual insecticide (its stability, very low water solubility and high lipid solubility) result in its accumulation in the fatty or lipid tissues of animals and are responsible for its ecological manification in carnivorous animals at the upper ends of food chains. The problems of the biological accumulation of DDT are intensified by its enzymatic metabolic conversion to the even more stable dehydrochlorination product, DDE, 1,1-dichloro-2,2-bis-(p-chloro-phyenyl)ethylene, which is a major environmental pollutant.

The drug metabolizing or multifunction oxidase (MFO) enzymes are known to play a dominant role in determining the absolute toxicity of insecticides to both insects and higher animals. DDT and its metabolic derivatives DDE and DDD (or TDE), 1,1-dichloro 2,2-bis-(p-chlorophenyl) ethane are all highly resistant to detoxication by MFO enzymes and this single factor accounts for their storage and accumulation in animal tissues, especially at the higher ends of food chains. On the other hand, certain known symmetrical DDT analogues such as methoxychlor, 1,1,1-trichloro-2,2-bis-(p methoxyphenyl)ethane and methiochlor, 1,1,1-trichloro-2,2-bis-(p methiophenyl)ethane, are readily attacked by MFO enzymes which metabolically convert or biodegrade such analogues, into environmentally acceptable products, rapidly eliminated by animals. Thus, methoxychlor is an example of a persistent but biodegradable insecticide which does not generally accumulate in animal tissues and is a more prudent choice than DDT for a variety of uses where environmental pollution is an important factor. However, methoxychlor and other known symmetrical DDT analogues (e.g., methylchor, 1,1,1-trichloro-2,2-bis (p methylphenyl)ethane or methiochlor) while exhibiting satisfactory insecticidal activity toward certain species of insects, exhibit considerably less insecticidal activity than DDT towards other species of insects. Thus, there exists a need for improved, persistent insecticides which manifest insecticidal activity levels about comparable to DDT, but which can also be metabolically biodegraded so as to prevent their accumulation in animals, particularily vertebrata, e.g. birds, fish and mammals.

DESCRIPTION OF THE INVENTION

We have found from metabolic studies in insects, mice, and in a model ecosystem with several food chains that certain asymmetrical DDT analogues with substituent groups readily attacked by multifunction oxidase (MFO) enzymes are substantially biodegradable and do not appear to be stored readily in animal tissues or concentrated in food chains. Insecticidal activity studies involving flies and mosquitoes have further indicated that the DDT analogues of this invention are persistent, biodegradable insecticides, of very low mammalian toxicity. The present invention thus provides compositions which are effective and persistent insecticides in inanimate situations; yet, when such compositions are absorbed into living organims they contain one or more points readily suceptible for attack by the MFO enzymes, promoting rapid detoxication of the insecticide. Such compositions have many advantages as safe, relatively stable, and potentially inexpensive residual insecticides. As employed herein the terms "DDT analogue" or "DDT type" are used synonymously to mean insecticides which comprise p-p' disubstituted diaryl trichloroethanes. The asymmetrical DDT analogues of the present invention contain at least one p-substitutent group such as methoxy (—CH$_3$O), methio (—SCH$_3$) or methyl (—CH$_3$) which in the presence of MFO enzymes acts as a substrate for MFO enzymes and thereby biodegrades or metabolically converts such analogues into environmentally acceptable products. The compositions also contain a second, different, p- substituent group which at least in part contributes to the insecticidal activity and/or the relatively low mammalian toxicity exhibited by the compositions of the present invention and may also contribute to their biodegradability.

We have further found that the asymmetrical DDT analogues having the following formula, and believed to be new compositions, are highly insecticidal, yet biodradable when contacted by MFO enzymes and thus of low toxicity to mammals:

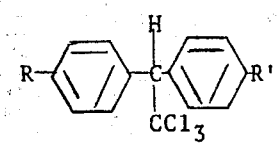

where R and R' are different and R is selected from the group consisting of —CH$_3$, —CH$_3$O, —C$_2$H$_5$O, —C$_3$H$_7$O and R' is selected from the group consisting of —SCH$_3$ and —CH$_3$.

The preparation of synthesis of the asymmetrical DDT analogues of the present invention can be accomplished by Bayer or Friedel Crafts condensation reactions between chloral and the appropriate substituted benzenes, for example, toluene, thioanisole, alkoxybenzenes, etc. The following Example I will illustrate the preparation of 2-(p-methoxphenyl)-2-(p-methylthiophenyl)-1,1,1-trichloro ethane.

EXAMPLE I

To 100 ml. of chloroform in an erlenmeyer flask cooled at 4° C, was added 5.32 g. (0.04 mole) of anhydrous AlCl$_3$. The contents of the flask were stirred for 10 minutes and a mixture of 10.2 g. p-methoxyphenyl-1,1,1-trichloro-methyl carbinol (U.S. P.2, 719, 865 Oct. 4, 1955), 7.5g. of thioanisole, and 25 ml. of chloroform, was added dropwise over 10 minutes. The contents were stirred for a further 5 minutes, allowed to come to room temperature and stirred overnight. The mixture was then poured over an ice-HCl mixture, steam distilled for 1 hour to remove chloroform and unreacted thioanisole, extracted with diethyl ether, and dried over anhydrous Na$_2$SO$_4$. Evaporation of the ether gave 14.5 g. (95%) yield of 2-(p-methoxyphenyl)-2-(p-methylthiophenyl)-1,1,1-trichloroethane, which after two recrystallizations from boiling methanol gave white, pleasant smelling crystals m.p. 94° C. NMR showed CH$_3$S protons at 7.55T., CH$_3$O protons at 6.20T, -H at 5.02T. fully confirming the structure. Using techniques similar to those employed in Example I the other compositions shown in Table I were prepared.

TABLE I

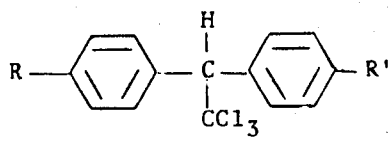

| Example No. | R | R' | m.p.°c |
|---|---|---|---|
| I | —CH$_3$O | —SCH$_3$ | 94 |
| II | —C$_2$H$_5$O | —SCH$_3$ | 103–4 |
| III | —CH$_3$O | —CH$_3$ | 80 |
| IV | —C$_2$H$_5$O | —CH$_3$ | 96 |
| V | —C$_3$H$_7$O | —CH$_3$ | 77 |
| VI | —C$_2$H$_5$ | —CH$_3$ | liquid |

Compositions of the present invention were tested for insecticidal activities determined by standard methods, and compared with the activities of DDT and other symmetrical analogues of DDT, e.g. methoxychlor. In these tests, female house flies, Musca domestica, under CO$_2$ anesthesia, were treated with topical application of 1 ul drops of w/v solutions of the insecticides in acetone. Three replicates of 20 flies 2–4 days old were treated on the pronotum at each dosage, and at least 5 dosages were used to establish each dosage versus mortality curve. Mortalities were determined by holding the flies at 72° F. (22°C.) with 40% sucrose solution as food. Topical applications were made to both susceptible (SNAIDM) and DDT-resistant (Rsp) strains in exactly the same manner. The results of these evaluations are reported in Table II as LD$_{50}$ values in ug. of toxicant per gram of insect using the average weight of the house fly as 20 mg. Evaluations of the toxicity of the same compositions to the larvae of the mosquitoes *Culex pipiens quinquefasciatus* and *Anopheles albimanus* were made as described by WHO (VBC/1968) and the results are also shown in Table II.

TABLE II

Comparison of Toxicity of New Unsymmetrical DDT Analogues to DDT and Methoxychlor

| Compound | topical LD$_{50}$female housefly µg/g. Susceptible | DDT-resistant | LC$_{50}$-ppm mosquito larvae | |
|---|---|---|---|---|
| | | | *Culex pipiens quinquefasciatus* | *Anopheles alpimanus* |
| DDT | 14.0 | 170 | 0.07 | 0.016 |
| Methoxychlor | 45.0 | 48 | 0.067 | 0.18 |
| Example I | 23.5 | 80 | 0.11 | 0.044 |
| Example II | 32.0 | 85 | 0.07 | 0.054 |
| Example III | 23.5 | 62.5 | 0.085 | 0.12 |
| Example IV | 9.0 | 27.0 | 0.13 | 0.11 |
| Example V | 20.0 | 55.0 | 0.04 | 0.20 |
| Example VI | 11.0 | 28.0 | 0.08 | 0.23 |

The results shown in Table II indicate that the exemplified compositions of the present invention are all more active than methoxychlor with respect to susceptible houseflies and all of said compositions are considerably more active than DDT with respect to DDT-resistant houseflies. Moreover, the compositions of the present invention are shown to be, in general, comparable to or more active than DDT and/or methoxychlor with respect to mosquito larvae.

Mammalian toxicity studies of the compositions of the present invention were conducted with female Swiss mice, six to eight weeks old. In these studies compositions were dissolved in olive oil at 5 to 10% w/v and the requisite dosage administered orally by a micrometer driven Hamilton syringe. The mice were observed for symptoms of intoxication and for mortality over a one week period. The results of these studies are shown in Table III.

TABLE III

| MOUSE TOXICITY | |
|---|---|
| Compound | Oral LD$_{50}$ mg/g. |
| DDT | 200 |
| Example I | 1000 |
| Example II | 1000 |
| Example III | 1000 |
| Example IV | 1000 |
| Example V | 500 |

The results in Table III indicate that the exemplified compositions of the present invention are less toxic than DDT with respect to oral administrations to mice. These studies further indicated that compositions containing a single methoxy, methyl, or methylthio group are of low mammalian toxicity but nevertheless highly insecticidal, making such compositions selectively insecticidal. It is believed that this selective insecticidal activity is a result of the generally higher concentration of MFO enzymes found in mammals as compared to insects.

MODEL ECOSYSTEM

A model ecosystem with several food chains was developed and can be used for evaluating pesticide biodegradability. The model consists of a 10 × 12 × 18 in. glass aquarium containing a shelf of 15 kg. of washed white quartz sand which is molded into a sloping soil-air-water interface. The lower portion is covered by 12 liters of "standard reference water" which provides satisfactory mineral nutrition for the growth of Sorghum halpense on the aerial portion, and the algae Oedogonium cardiacum in the aquatic portion. The latter is seeded with a compliment of plankton, and contains Daphnia magna and Physa snails. The aquarium is provided with aeration and is kept in an environmental plant growth chamber at 80° F (26° C) with 12 hr daylight exposure to 5000 ft-candles.

In operation, the Sorghum seeds are planted and the aquarium allowed to equilibrate for 20 days until the Sorghum plants are about 6 in. high. The leaves are then treated with 5.0 mg. of the radiolabeled pesticide compound of interest in acetone applied through a micropipette so that only the plant surface is contaminated. Ten large Estigmene acrea larvae are placed in the chamber and allowed to feed until the plants are consumed. The radiolabeled fecal materials thoroughly contaminate the aqueous portion and are taken up into the several food chains. After 26 days, 300 Culex quinquefasciatus mosquito larvae are added to the chamber, and after 30 days three Cambusia affinis fish are added. The experiment is terminated after 33 days, when weighed samples of fish, snails, mosquito larvae, algae, and water are removed and assayed to total radioactivity. These samples are homogenized and extracted with diethyl ether, and both water and ether layers examined by tlc to determine the qualitative and quantitative nature of the degradative products present, using radioautography and serial scintillation counting of the areas containing radioautography. The results of the total examination of the model eco system provide evidence of the relative biodegradability of the pesticide. Using such a model ecosystem with DDT as the pesticide confirms that DDT is not biodegradable but rather, manifests a substantial magnification of concentration in the food chain organisms. In contrast, when p-p' disubstituted diaryl trichloroethane insecticides which contain at least one p-substituent group readily susceptible to attack by MFO enzymes (e.g. $-CH_3$, $-CH_3O$, $SCH_3$) are evaluated in the model they are found to be biodegradable in that there is little or no magnification of concentration of such insecticides in the food chain organisms.

The compositions of the present invention can be formulated into insecticidal formulations using techniques known in the art, for example, in formulating DDT insecticides. Thus, dusts, water dispersions, emulsions and/or solutions can be formulated provided the carrier or solvent is compatible and inert in the sense that it does not react or interfere with the insecticidal and biodegradable characteristics.

While the present invention has been described by reference to illustrative examples various modifications will be apparent to those skilled in the art and any such modifications are intended to be within the spirit and scope of the invention as defined by the appended claims.

What is claimed is:

1. A biodegradable insecticidal formulation comprising a major amount of a compatible inert carrier and a minor amount sufficient to provide insecticidal activity of a compound having the formula:

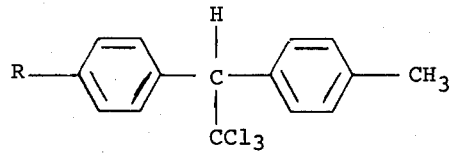

where R is selected from the group consisting of $-OCH_3$, $-OC_2H_5$ and $-OC_3H_7$.

2. A formulation as defined by claim 1 wherein R is $-OCH_3$.

3. A formulation as defined by claim 1 wherein R is $-OC_2H_5$.

4. A formulation as defined by claim 1 wherein R is $-OC_3H_7$.

* * * * *